United States Patent [19]

Stutz, Jr.

[11] Patent Number: 5,082,453

[45] Date of Patent: Jan. 21, 1992

[54] MULTI-CONTACT CONNECTOR SYSTEM FOR AN IMPLANTABLE MEDICAL DEVICE

[75] Inventor: William H. Stutz, Jr., Burbank, Calif.

[73] Assignee: Siemens-Pacesetter, Inc., Sylmar, Calif.

[21] Appl. No.: 701,283

[22] Filed: May 16, 1991

[51] Int. Cl.[5] ..................... H10R 13/62; H10R 13/15
[52] U.S. Cl. .................................... 439/265; 439/592
[58] Field of Search ............. 439/259, 263, 265, 586, 439/587, 592, 593, 601

[56] References Cited

U.S. PATENT DOCUMENTS

| | | | |
|---|---|---|---|
| 2,049,093 | 7/1936 | Thorin | 173/361 |
| 2,202,315 | 5/1940 | Langdon | 439/592 |
| 2,749,526 | 6/1956 | Petersen | 339/61 |
| 2,824,183 | 2/1958 | Marasco et al. | 200/51.09 |
| 2,829,357 | 4/1958 | Lorch et al. | 339/61 |
| 3,153,561 | 10/1964 | Cooney | 439/592 |
| 3,509,296 | 4/1970 | Harshman et al. | 200/46 |
| 3,952,173 | 4/1976 | Tsuji et al. | 200/264 |
| 4,614,390 | 9/1986 | Baker | 439/592 |
| 4,712,557 | 12/1987 | Harris | 439/586 |
| 4,978,306 | 12/1990 | Robb | 439/8 |

FOREIGN PATENT DOCUMENTS 3137288 3/1983 Fed. Rep. of Germany .
0137577 5/1989 Japan .................. 439/259

*Primary Examiner*—David L. Pirlot
*Assistant Examiner*—Hien D. Vu
*Attorney, Agent, or Firm*—Lisa P. Weinberg

[57] ABSTRACT

A multi-contact connector system for electrically and mechanically connecting a lead for the delivery of electrical energy at a body site to an implantable source of the electrical energy includes a plug connector element carried at a proximal end of the lead which is received in a socket connector element carried on the source of electrical energy. The plug connector element is a radially expandable sleeve with a number of exteriorly exposed contacts respectively connected to conductors contained within the lead. Corresponding contacts are mounted in the interior of the socket connector element. The plug connector sleeve fits over a flexible expansion element contained in the socket connector element. The expansion element is operated by a toggle switch after the connector elements are engaged so as to radially expand. The sleeve of the plug connector element on which the contacts are carried is also radially expanded, so that the contacts on the connector elements are forced into tight engagement when the expansion element is actuated.

10 Claims, 2 Drawing Sheets

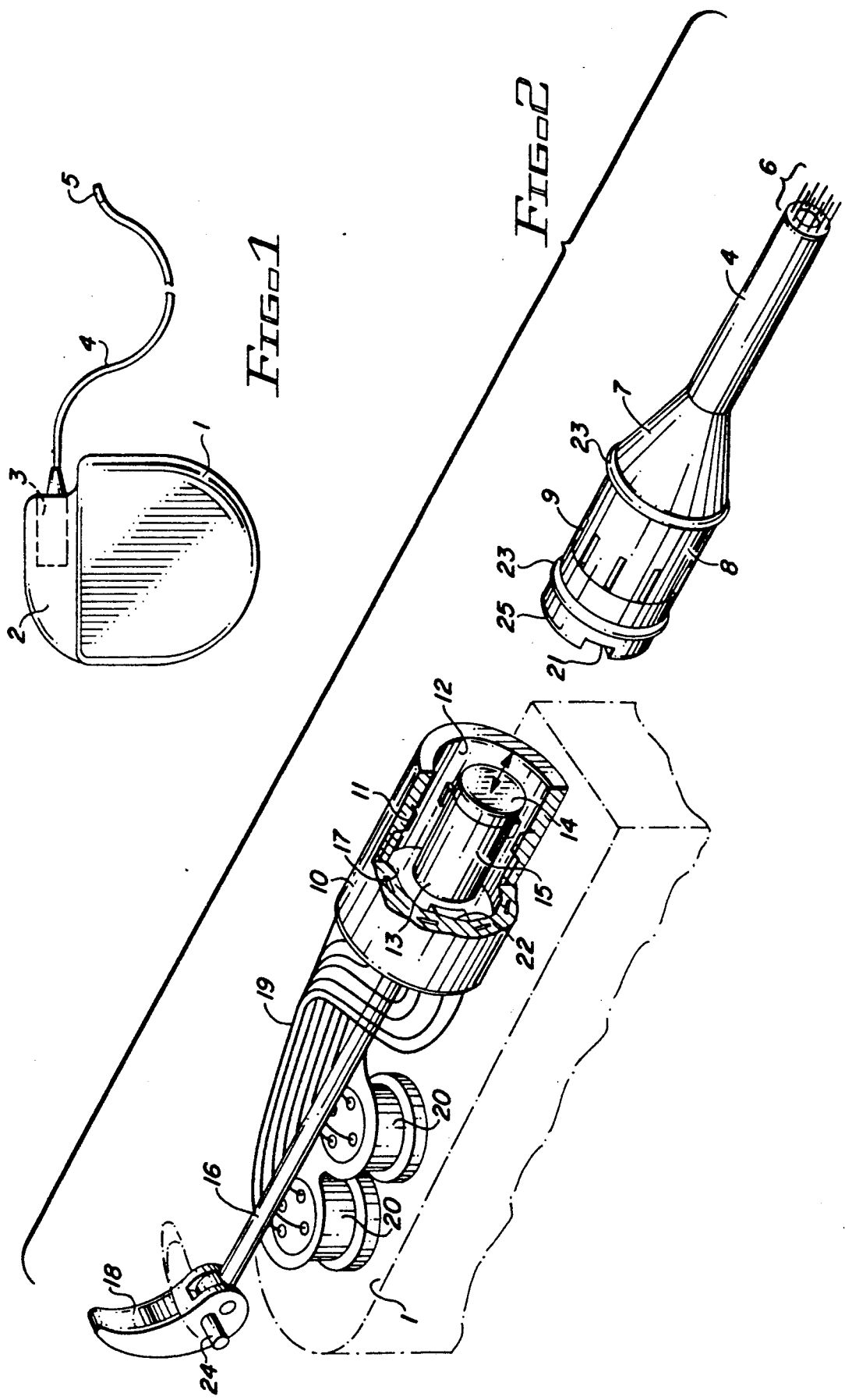

MULTI-CONTACT CONNECTOR SYSTEM FOR AN IMPLANTABLE MEDICAL DEVICE

BACKGROUND OF THE INVENTION

1. Field of the Invention

The present invention is directed to a connector system for mechanically and electrically connecting a lead in a medical device for delivering electrical energy to a body site from an implantable source for the electrical energy, such as for connecting a pacing lead to an implantable pulse generator in an implantable pacing system.

2. Description of the Prior Art

In implantable medical devices, which are for the purpose of delivering electrical energy to a body site, such as the heart, a flexible lead is used to conduct the electrical energy from an implanted source of the electrical energy to the body site. The lead delivers the electrical energy at a free end thereof. The opposite end of the lead must be mechanically and electrically connected to the housing containing the source of electrical energy. Since the system is intended for in vivo implantation in a patient, the connection system in such devices must not only provide reliable mechanical and electrical connection, but also must do so in a manner which does not significantly add to the size of the implanted system, and which seals from body fluids the actual location at which the electrical connection occurs.

In the case of a heart pacemaker, for example, the lead may be used to carry conductors which serve a purpose other than delivery of the therapeutic electrical energy. For example, in sophisticated pacemakers of the type currently available, one or more sensors may be disposed in the pacing lead for detecting various physiological characteristics. Each sensor has at least one conductor associated therewith which must be contained within the pacing lead and also electrically connected to an appropriate contact at the housing, so that the electrical signals corresponding to the sensed physiological characteristic can be used by logic circuitry within the housing to control the pacing rate, the amplitude and duration of the pacing pulses, and other attributes of the pacing therapy.

It is a problem in the implantable medical device technology to provide a reliable mechanical and electrical connector which can accommodate a relatively large number of electrical contacts without significantly adding to the size of the connector.

A further problem in the implantable medical device technology is to minimize the insertion force required to insert the lead plug into the housing socket. Typically, a lead is by design very flexible and the lead plug on the lead does not protrude much beyond the pacer body when the lead is inserted into the housing socket. Accordingly, it is rather difficult to insert the flexible male lead into the female connector. Compounding the problem in multiple contact systems is the high insertion force required due to the accumulated resistive effects of spring contacts and fluid isolation seals.

Various types of connector or plug assemblies (not necessarily for implantable medical devices) are known in the art which make use of a resilient or deformable component within the assembly to effect electrical connection of other components. For example, a multicontact connector is disclosed in U.S. Pat. No. 2,749,526 wherein the plug and socket connector elements have complementary conical shapes, and the contacts are in the shape of barbs so that a relatively large contact area is presented by each contact for mating with its counterpart. The contacts are held in elastic plug and socket members, so that the elements can be tightened together sufficiently to insure proper electrical connection. A compression joint for an electrical connector which is also deformable when the two connector elements are tightened together is disclosed in U.S. Pat. No. 2,829,357.

Switches having deformable, elastic contact elements with electrically conductive particles embedded therein are disclosed in U.S. Pat. Nos. 3,509,296 and 3,952,173. When the contact elements are compressed and deformed, the particles move closer together causing the element to become conductive, or increase in conductivity.

A snap-together universal electrical connection is disclosed in U.S. Pat. No. 4,978,306, wherein a spherical plug is snapped into a spherical socket so as to rotate and swivel therein. Contact elements are disposed at selected locations on the respective surfaces of the plug and socket so that electrical connections are made and broken as the plug is moved within the socket.

A cable connector is disclosed in U.S. Pat. No. 2,824,183 having two pairs of contact elements which are normally maintained spaced apart by resilient concave walls in which the contact elements are respectively mounted. The contact elements so mounted are contained within a socket, with the contacts being forced together by the insertion of a plug in the socket, the prongs of the plug causing the elastic walls to deform and force the contacts together.

A connector is disclosed in Japanese Application No. 62-29634 wherein a male connector element has a number of axially extending flexible carriers each having a contact at a free end thereof. The carriers surround a circular plate movable by a pusher rod. The male connector element is loosely inserted in a female connector element, and the rod is pushed so that the plate causes the carriers to move radially outward, forcing the contacts into connection with corresponding contacts carried on the interior of the female connector element.

A switch assembly is disclosed in German OS 31 37 288 wherein a resilient ball element is contained within a housing, the ball element containing particulate electrical conductors. When an actuator element is pressed, the ball is flattened so that its circumference touches a cylindrical contact surrounding the ball. The particulate conductor embedded within the ball thereby causes an electrical connection to be made.

Lastly, a locking electrical outlet plug is disclosed in U.S. Pat. No. 2,049,093, wherein the plug has an actuator rod with a free end that is inserted into the socket adjacent one of the blades of the plug. After the plug is inserted in the socket, the actuator can be pushed to force the free end tightly between the plug blade and a wall of the blade receptacle in the socket to hold the plug tightly in the socket. The actuator can be released when removal of the plug is desired.

None of these known types of plug assemblies is specifically designed or intended for use in an implantable medical device, such as a heart pacemaker. Therefore, none of these known devices address the problems associated with implanted medical devices of maintaining a small size while accommodating a large number of contacts and being impervious to, and isolated from, the action of body fluids, and of achieving reliable long-term electrical and mechanical connections with a small insertion force.

SUMMARY OF THE INVENTION

It is an object of the present invention to provide a connector assembly for an implantable medical device which has a large number of electrical contacts but which does not occupy significantly more volume than conventional contact assemblies accommodating a lower number of contacts.

It is a further object of the present invention to provide such a connector assembly which is easy to engage on installation and which is resistant to inadvertent disengagement while being easily disengaged when required.

It is a further object of the present invention to provide such a connector assembly which is impervious to body fluids when implanted. Moreover, the invention is capable of maintaining fluid seals between adjacent contacts as well as preventing fluids from entering the connector.

The above objects are achieved in accordance with the principles of the present invention in a connector assembly wherein a distal end of a lead used to deliver electrical therapy to a site in the body has a plug in the form of a hollow sleeve with a plurality of electrical contacts disposed circumferentially around the exterior of the sleeve. The electrical contacts are respectively connected to electrical conductors contained within the lead. The sleeve of the plug consists of elastic material which is deformable so as to expand radially outwardly.

A socket is carried on the portion of the medical device serving as the source for electrical energy, which is also implantable in a patient. The socket is also in the form of a sleeve, but is substantially nonyielding in the radial direction. The socket sleeve is keyed to the plug and has a plurality of electrical contacts mounted circumferentially at the interior surface thereof and arranged in accordance with the keying so as to be disposed respectively adjacent the contacts on the plug when the plug is inserted in the socket. The socket also includes a centrally disposed expansion device which is received in the interior of the plug sleeve when the plug is inserted in the socket. The outer diameter of the sleeve of the plug is slightly smaller than the inner diameter of the socket sleeve, so that when the plug is initially inserted into the socket, it is an easy slip fit requiring essentially no insertion force. The expansion device is then actuated so as to radially expand, which also causes the sleeve of the plug to radially expand, thereby forcing the contacts carried on the exterior of the plug sleeve into contact with the respective contacts carried on the interior of the socket sleeve as well as forcing sealing surfaces into intimate contact along with mechanical retention of the lead connector.

The plug may be provided with integral O-ring seals disposed on opposite sides of the contacts at the exterior of the plug sleeve, to provide a seal against body fluids entering the contact location.

The expandable device may be formed by a rod operated at one end by a toggle switch so as to be movable longitudinally back and forth. The rod terminates in a shouldered head inside the socket sleeve and a flexible expansion sleeve is disposed between the shouldered head and the rear of the socket. When the toggle switch is actuated, the rod is moved in a direction causing the shouldered head to be pulled closer to the rear wall of the socket, thereby causing the expansion sleeve disposed therebetween to slightly buckle and assume a barrel-shape. The expansion sleeve thus has a larger outer diameter in this contracted position than in its relaxed position, and forces the plug sleeve radially outwardly as described above.

The above-described device is advantageously designed so as to be capable of withstanding constant and long-term flexing and/or tugging that the connector might undergo due to heart "pump" movement.

DESCRIPTION OF THE DRAWINGS

FIG. 1 is a side view of a heart pacemaker of the type in which a connector assembly constructed in accordance with the principles of the present invention may be used.

FIG. 2 is a perspective view, partly broken away, of the disengaged plug and socket of a connector assembly constructed in accordance with the principles of the present invention.

DESCRIPTION OF THE PREFERRED EMBODIMENTS

Figure 3:
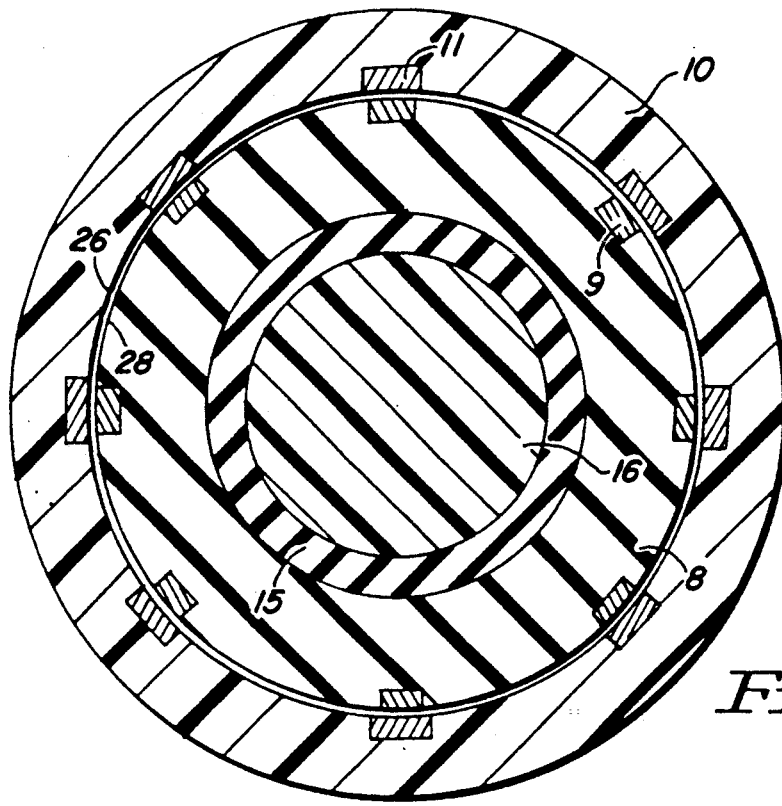
FIG. 3 is a sectional view of an engaged plug and socket of the connector assembly constructed in accordance with the principles of the present invention, prior to actuation of the expansion device.

The basic elements of a medical device, namely a heart pacemaker, in which the connector assembly disclosed below may be used, are shown in FIG. 1 It will be understood that the connector assembly may be used to advantage in any type of implantable medical device wherein a mechanical and electrical connection must be made, and the connector assembly described below is shown in the context of a pacemaker only as an example. The pacemaker includes a housing 1, which contains a battery and integrated electrical circuitry of the type known to those skilled in the art for performing a variety of functions. The battery serves to power the electrical circuitry, as well as serving as a source for the electrical therapy which is administered by the device. The housing 1 consists of metal, and has a connector portion 2 at a top thereof, consisting of a transparent, dimensionally stable, hermetic encapsulation, such as epoxy, which encapsulates a number of components not shown in detail in FIG 1, but shown in the figures below. The connector portion 2 contains a connector assembly 3, shown in FIG. 1 in an engaged condition, for mechanically and electrically connecting the proximal end of a lead 4 to the housing 1. The lead 4 terminates in a distal end 5, at which pacing electrodes and/or physiological sensors are disposed.

As shown in greater detail in FIG. 2, the pacing electrodes and sensors have a plurality of conductors 6 respectively connected thereto. These conductors are accommodated through the lead 4 and respectively terminate in a plurality of exposed contacts 9. The contacts 9 are carried on the exterior surface of a plug sleeve 8, which is joined to the lead 4 by a conically expanding section 7. The sleeve 8, the section 7 and the lead 4 (with the exception of the electrical conductors therein) all consist of flexible insulating material, such as silicone.

A free end 25 of the plug sleeve 8 has a keyway 21 therein.

The exposed contacts 9 are circumferentially arranged around the exterior surface of the plug sleeve 8. Integral O-rings 23 are also disposed on the exterior of the sleeve 8 on opposite sides of the exposed contacts 9.

A connector socket 10 and related components are disposed at a top of the housing shown in dashed lines in FIG. 2. The encapsulated portion of the connector portion 2 has been removed for clarity. The socket 10 is in the form of a sleeve having a cylindrical interior opening 12 having an interior surface with a plurality of exposed contacts 11 disposed therein. Each contact 11 is intended to mate and make an electrical connection with one of the respective exposed contacts 9 on the plug sleeve 8, when the plug is inserted in the socket 10. The contacts 11 are electrically connected to respective individual conductors in a ribbon conductor 19, which is in turn electrically connected to feedthroughs 20. Connections (not shown) in the interior of the housing 1 are made at the opposite sides of the feedthroughs 20 to the electrical components contained within the housing 1.

The socket 10 is provided with a key 22 at a rear thereof. When the plug is inserted in the socket 10 so that the key 22 and the keyway 21 are engaged, the contacts 9 on the plug sleeve 8 will be aligned with the contacts on the interior of the socket 10. (Alternatively, the key may be on the plug sleeve 8 and the keyway in the socket 10.)

The socket 10 consists of substantially nonyielding plastic material, such as polysulfone.

An expansion device 13 is disposed in the interior opening of the socket 10. The expansion device 13 fits loosely inside the plug sleeve 8 when the plug sleeve 8 is inserted in the socket 10. In the embodiment shown in FIG. 2, the expansion device is formed by a shouldered head 14, which is longitudinally movable back and forth in the directions of the double arrow by an actuation rod 16. The rod 16 is movable back and forth by a toggle actuator 18, mounted in the transparent dimensionally stable hermetic encapsulation by a toggle pin 24. The expansion device also includes an expansion sleeve 15 disposed between the shouldered head 14 and a rear wall 17 of the socket 10. The expansion sleeve 15 consists of flexible, deformable material, such as silicone. The sleeve 15 is shown in its substantially tubular, relaxed condition in solid lines in FIG. 2. When the toggle switch 18 is actuated to the dashed line position shown in FIG. 2, the actuator rod 16 causes the shouldered head 14 to move toward the rear wall 17, thereby causing the expansion sleeve 15 to slightly buckle, and to assume the barrel shape indicated by dashed lines in FIG. 2. The barrel shape has a larger outer diameter than the relaxed shape of the expansion sleeve 15.

The radial expansion of the sleeve 15 causes a similar radial expansion of the flexible plug sleeve 8, thereby forcing the contacts 9 into tight adjacency with the contacts 11 as well as forcing the sealing surfaces 26 (shown in FIG. 3) between contacts 11 to expand into intimate contact with the sealing surfaces 28 (shown in FIG. 3) between contacts 9. The integral O-rings 23 disposed on opposite sides of the contact 9 completely seal both sides of the contacts 9 from the intrusion of body fluids.

A sectional view of the engaged plug sleeve 8 and socket 10, before actuation of the expansion device 13, is shown in FIG. 3. (The actuator rod 16 is also shown in section with standard hatching to indicate the plastic composition thereof, but it is to be understood that the composition could also be formed of metal. The plug sleeve 8 is shown in FIG. 3 with thick-lined hatching to indicate it is a flexible and deformable elastomer. The socket 10 is shown with standard hatching for plastic, to indicate that it is substantially nonyielding, at least radially. As can be seen in FIG. 3, when the plug sleeve 8 is initially inserted in the socket 10, the contacts 9 and 11 are in radial registry and are spaced from each other. (The rear O-ring 23 has been omitted in FIG. 3 for clarity.)

Figure 4:
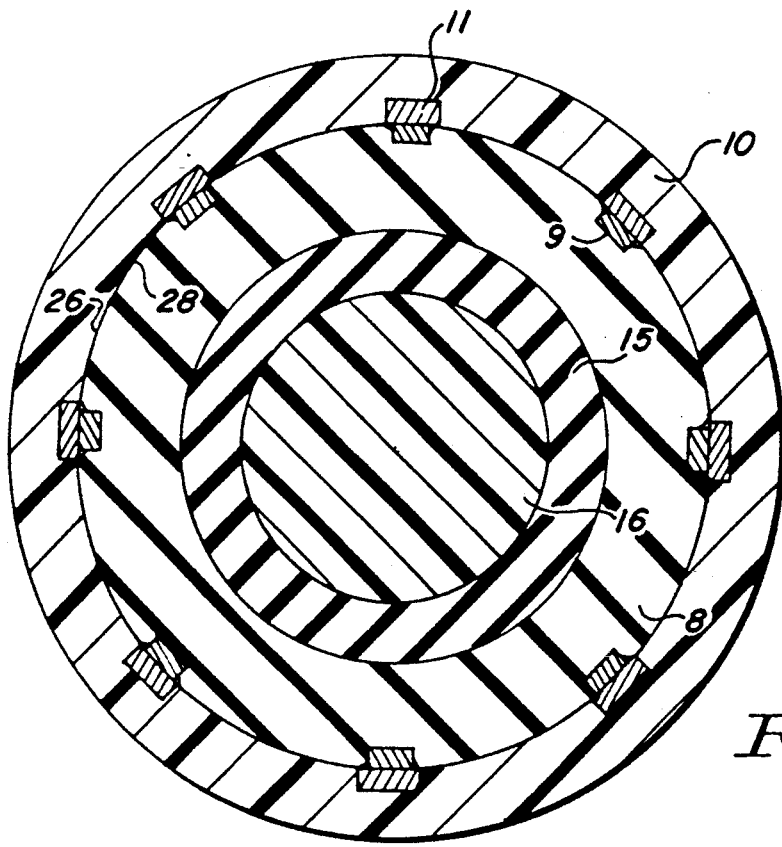
FIG. 4 is a sectional view of the engaged socket and plug of a connector assembly constructed in accordance with the principles of the present invention, after actuation of the expansion device.

FIG. 4 shows the same view as FIG. 3, but after the expansion device 13 has been actuated. The actuation of expansion device 13 causes the sleeve 15 to radially expand, as shown in FIG. 4. The portion in section of the sleeve 15 which can be seen in FIG. 4 has also been shown hatched with thick lines to indicate the flexible and deformable nature of the sleeve 15. The radial expansion of the sleeve 15 has caused the plug sleeve 8 to similarly radially expand, so that the various pairs of contacts 9 and 11 are maintained tightly together.

If disengagement of the plug and socket is desired, the toggle 18 can be returned to the position shown in solid lines in FIG. 2, thereby returning the device 13 to its relaxed condition, and permitting withdrawal of the plug from the socket 10.

Because the plug sleeve 8 is initially inserted only loosely into the socket 10, there is virtually no insertion force required to initially engage the connector assembly.

Although modifications and changes may be suggested by those skilled in the art, it is the intention of the inventor to embody within the patent warranted hereon all changes and modifications as reasonably and properly come within the scope of his contribution to the art.

What is claimed is:

1. A multi-contact connector assembly for an implantable medical device, said device having a housing for a source of electrical energy and electronic circuitry, and a lead for delivering said electrical energy in vivo from said housing to a body site, said connector assembly comprising:

a hollow, radially expandable plug connected to said lead having a plurality of contacts on an exterior surface thereof;

a socket carried on said housing having a plurality of contacts on an interior surface thereof, said socket having dimensions for loosely receiving said plug with said contacts on said plug in spaced radial registry with said contacts on said interior surface of said sleeve; and actuatable means disposed in said socket, and received in said plug when said plug is received in said socket, for radially expanding said plug for respectively mechanically and electrically connecting said contacts on said plug with said contacts on said interior surface of said socket.

2. A connector assembly, as claimed in claim 1, further comprising keying means having first and second engageable elements respectively carried on said plug and said socket for placing said contacts on said plug and in said socket in radial registry when said plug is inserted in said socket.

3. A connector assembly, as claimed in claim 1, wherein said actuatable means is a flexible sleeve, with means disposed in said flexible sleeve for radially expanding said sleeve.

4. A connector assembly, as claimed in claim 3, wherein said means for radially expanding said sleeve is a means for buckling said sleeve to increase the outer diameter thereof.

5. A connector assembly, as claimed in claim 4, wherein said socket has a rear wall, and wherein said means for buckling said sleeve is a toggle-actuated, longitudinally movable rod terminating in a shouldered head, with said flexible sleeve disposed between said shouldered head and said rear wall of said socket, with actuation of said rod by said toggle causing said shouldered head to move toward said rear wall and thereby cause said sleeve to buckle.

6. A multi-contact connector assembly for an implantable medical device, said device having a housing for a source of electrical energy and electronic circuitry, and a lead for delivering said electrical energy in vivo from said housing to a body site, said connector assembly comprising:

a plug connected to one end of said lead and a socket carried on said housing and shaped to receive said plug;

said plug having a radially expandable hollow sleeve, receivable in said socket, having an exterior surface with an outer diameter and a plurality of exposed electrical contacts thereon, said contacts being respectively electrically connected to conductors in said lead;

said socket having an interior surface with a plurality of exposed electrical contacts therein disposed to respectively mate with said contacts on said sleeve of said plug when said plug is received in said socket, said interior surface of said socket having a diameter larger than the outer diameter of said sleeve so that said contacts on said sleeve and on said interior surface are radially spaced from each other when said plug is inserted in said socket; and actuatable, radially expandable means mounted in said socket and received in said sleeve of said plug when said plug is inserted in said socket for, upon actuation of said expandable means, radially expanding said sleeve to bring said contacts on said sleeve into respective mechanical and electrical connection with said contacts on said interior surface of said socket, whereby body fluids are prevented from entering the connector assembly as well as being prevented from coming into contact with the engaged electrical contacts.

7. A connector assembly, as claimed in claim 6, further comprising keying means having first and second engageable elements respectively carried on said plug and said socket for placing said contacts on said plug and in said socket in radial registry when said plug is inserted in said socket.

8. A connector assembly, as claimed in claim 6, wherein said actuatable means is a flexible sleeve, with means disposed in said flexible sleeve for radially expanding said sleeve.

9. A connector assembly, as claimed in claim 8, wherein said means for radially expanding said sleeve is a means for buckling said sleeve to increase the outer diameter thereof.

10. A connector assembly, as claimed in claim 9, wherein said socket has a rear wall, and wherein said means for buckling said sleeve is a toggle-actuated, longitudinally movable rod terminating in a shouldered head, with said flexible sleeve disposed between said shouldered head and said rear wall of said socket, with actuation of said rod by said toggle causing said shouldered head to move toward said rear wall and thereby cause said sleeve to buckle.

* * * * *

UNITED STATES PATENT AND TRADEMARK OFFICE
CERTIFICATE OF CORRECTION

PATENT NO. : 5,082,453
DATED : Jan. 21, 1992
INVENTOR(S) : William H. Stutz, Jr.

It is certified that error appears in the above—identified patent and that said Letters Patent is hereby corrected as shown below:

On Col. 6, line 52, delete "sleeve" and insert therefor --socket--.

On Col. 7, line 24, delete "socket, having" and insert therefor --socket, said sleeve having--.

Signed and Sealed this

Twenty-fourth Day of August, 1993

Attest:

Attesting Officer

BRUCE LEHMAN

Commissioner of Patents and Trademarks